United States Patent [19]

Colpitts

[11]  4,360,344

[45]  Nov. 23, 1982

[54] COMPOSITE DENTURE COMBINING SOFT POLYURETHANE AND HARD POLYMER COMPONENTS

[75] Inventor: Ralph Colpitts, Chesterfield, Mo.

[73] Assignee: Polythetics, Inc., St. Louis, Mo.

[21] Appl. No.: 249,643

[22] Filed: Mar. 31, 1981

[51] Int. Cl.$^3$ ............................................. A61C 13/00
[52] U.S. Cl. .................................... 433/199; 433/171; 433/201
[58] Field of Search .................................. 264/16–18; 433/168, 171, 195, 199, 201

[56] References Cited

U.S. PATENT DOCUMENTS

| | | | |
|---|---|---|---|
| 3,251,910 | 5/1966 | Barnhart | 264/17 |
| 3,258,509 | 6/1966 | Barnhart | 264/17 |
| 3,659,344 | 5/1972 | Gavazzi | 433/168 |
| 4,024,636 | 5/1977 | Colpitts et al. | 32/2 |
| 4,024,637 | 5/1977 | Colpitts et al. | 32/2 |
| 4,080,412 | 3/1978 | Colpitts et al. | 264/17 |
| 4,225,696 | 9/1980 | Colpitts et al. | 433/199 |

*Primary Examiner*—Lorenzo B. Hayes
*Attorney, Agent, or Firm*—Scully, Scott, Murphy & Presser

[57]  ABSTRACT

An artificial denture of composite construction is provided which comprises a tooth-holding portion fabricated from a hard non-polyurethane polymer having a hardness of not less than about Shore D40 integrally chemically bonded to a mouth-engaging portion fabricated from a soft non-hydrophilic polyurethane elastomer having a hardness of not greater than about Shore A65, said polyurethane being the reaction product of a polyether polyol and an aliphatic, cycloaliphatic or aralkyl di- or polyisocyanate in which the isocyanate groups are directly bonded to the aliphatic, cycloaliphatic or alkyl moieties thereof.

7 Claims, No Drawings

COMPOSITE DENTURE COMBINING SOFT POLYURETHANE AND HARD POLYMER COMPONENTS

BACKGROUND OF THE INVENTION

1. Field of the Invention

This invention relates to the field of artificial dentures, and more particularly, to such dentures prepared from polyurethane elastomers and hard polymer components such as the hard acrylic resins and the hard epoxide resins.

2. Description of the Prior Art

It has been proposed to provide dentures with a soft layer in contact with the gums and other mouth parts to provide tissue relief. Such soft layers have been composed of acrylics, silicones, and similar rubber-like materials. But on aging, such soft layers tend to harden and give off undesirable odors. In addition, some decomposition of the polymer may also occur presumably due to an oxidation process as well as to pH fluctuations within the mouth. By way of overcoming these disadvantages, U.S. Pat. Nos. 4,024,636 and 4,080,412, both to Colpitts et al., and both incorporated by reference herein, describe dentures in which teeth are anchored in a gum member comprising a tooth-holding portion fabricated from a hard nonhydrophilic polyurethane elastomer having a hardness of not less than about Shore D40, and a mouth-engaging portion fabricated from a soft nonhydrophilic polyurethane elastomer having a hardness of not greater than about Shore A65 integrally and chemically bonded into a unitary mass. U.S. Pat. No. 4,024,637 to Colpitts which is also incorporated by reference herein describes a denture in which hard non-hydrophilic polyurethane elastomer teeth are imbedded in and chemically bonded to a soft non-hydrophilic polyurethane elastomer. Preferred non-hydrophilic elastomers are those formed by isocyanate-terminated prepolymers which are cross-linked or cured by mixing with a cross-linking agent and heating as required to effect curing. Isocyanate-terminated prepolymers suitable for preparing the hard non-hydrophilic polyurethane elastomers are prepared by the reaction of polyether diols or triols with aliphatic or cycloaliphatic or aralkyl di- or polyisocyanates in proportion to give free NCO groups. The prepolymers are then cured or cross-linked with a diol, polyol, an alkanolamine, a diamine or a tertiary amine containing polyol, or blends thereof. Advantageously, the diol or polyol is a polyether diol or polyol or a hydroxyl-terminated prepolymer.

By way of improving the resistance of polyurethane dentures to mechanical distortion or flex under the conditions prevailing in the mouth, U.S. Pat. No. 4,225,696 to Colpitts, et al., which additionally is incorporated by reference herein, substitutes the aforementioned aliphatic, cycloaliphatic or aralkyl di- or polyisocyanates with aromatic polyisocyanates in which the isocyanate groups are bonded directly to the aromatic nucleus, e.g., 2,4-tolylene diisocyanate (TDI), isomeric mixtures of TDI, 3,3'-tolidene 4,4'-diisocyanate (TODI), 3,3'-dimethyldiphenylmethane 4,4'-diisocyanate, diphenylmethane 4,4'-diisocyanate (MDI), mixtures of MDI and adducts of MDI, etc. The resulting polyurethane can be fabricated into the soft, mouth-engaging portion of a denture possessing a relatively hard polymer as the tooth-engaging portion thereof. The hard polymer can be a hard polyurethane prepared in accordance with any of the aforesaid Colpitts, et al., patents or it can be any of the hard polymers heretofore used in the making of dentures. As is well known, the acrylics, a class of relatively hard resins, have for many years been used in the manufacture of prosthodontic devices and would be prime candidates for preparing composite polyurethane/hard polymer dentures in accordance with the teachings of U.S. Pat. No. 4,225,696 to Colpitts, et al. However, as desirable an improvement as such composite dentures are, their polyurethane components which, as previously stated, are prepared from an aromatic isocyanate such as TDI, TODI or MDI, are relatively photosensitive and prone to degradation by actinic radiation. The probable explanation of this behavior is that when an isocyanate group reacts with water, it forms a urea group which, in the case of the aromatic isocyanates, is relatively chemically stable but light sensitive.

Accordingly, it is desirable to provide a denture which has a soft, mouth-engaging element to provide for the wearer's comfort and which at the same time is resistant to flex and photodegradation.

SUMMARY OF THE INVENTION

In accordance with the present invention, an artificial denture of composite construction is provided which comprises a tooth-holding portion fabricated from a hard non-polyurethane polymer having a hardness of not less than about Shore D40 integrally chemically bonded to a mouth-engaging portion fabricated from a soft non-hydrophilic polyurethane elastomer having a hardness of not greater than about Shore A65, said polyurethane being the reaction product of a polyether polyol and an aliphatic, cycloaliphatic or aralkyl di- or polyisocyanate in which the isocyanate groups are directly bonded to the aliphatic, cycloaliphatic or alkyl moieties thereof.

The composite dentures of the present invention possess significant advantages over an all-polyurethane denture. Approximately 40% of all full and partial dentures currently being made possess acrylic teeth. Since in practice it is difficult to obtain a good chemical bond between acrylic teeth and polyurethane, the opportunities for debris (derived from foods, beverages, tobacco, etc.) to infiltrate crevices between the teeth and the polyurethane are much greater than in the case of acrylic teeth bonded to an acrylic tooth-holding portion. And since the hard acrylics as a class are generally quite stable to flex and are superior in this regard to an all-polyurethane denture whose mouth-engaging portion is prepared with an aliphatic, cycloaliphatic or aralkyl di- or polyisocyanate, it is particularly advantageous to mate the relatively flex-prone but photodegradation resistant soft polyurethanes as aforedescribed with the acrylics or, for that matter, with any other flex-resistant nonpolyurethane polymers such as the hard epoxide resins. The resistance of such polyurethanes to degradation under the influence of actinic radiation is probably due to the fact that unlike aromatic urea groups, the aliphatic urea groups of these polyurethanes (to the extent formed by reaction of some isocyanate groups with water) tend to react with each other to form biuret which is considerably more light resistant than aromatic urea groups which do not react to provide biuret in any appreciable amount. Yet another advantage of these polyurethanes over those prepared with aromatic isocyanates lies in the reduced incidence with which they form urea/biuret groups at all. More of the available isocyanate groups of an aliphatic isocyanate will react with the hydroxyl groups of the polyether polyol to form the desired urethane linkages (which confer chemical resistance) than would be the case with an aromatic isocyanate.

DESCRIPTION OF THE PREFERRED EMBODIMENTS

The tooth-holding portion of the composite denture herein can be prepared from among any of the known and conventional hard acrylic resins employed in the manufacture of dentures, e.g., those having a hardness of at least Shore D40 and up to about Shore D100. The term "acrylic resin" as used herein is intended to include homopolymers of acrylic esters and acrylic amides of the general formula

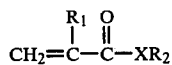

in which X is O or NH, $R_1$ is H or methyl and R is any of a wide variety of groups including aliphatic, cyclocloaliphatic, alkaryl, aralkyl, alkoxy, aryloxy, glycidyl, etc., groups, and copolymers of said esters/amides with other acrylic esters/amides and/or with one or more other copolymerizable ethylenically unsaturated monomers such as acrylonitrile, butadiene, styrene, vinyl acetate, and the like. Poly(methylmethacrylate) is an especially preferred resin for the tooth-holding portion of the composite denture herein because of the ready availability of the monomer, its low cost and its common use in dentistry. The techniques whereby acrylic resins can be fashioned into denture and partial dentures are well known, e.g., U.S. Pat. Nos. 3,251,910 and 3,258,509 to Barnhart both of which are incorporated by reference herein.

The hard epoxide resins, e.g., those having a hardness of at least Shore D40 and up to about Shore D100, which can be employed as the teeth-holding component of the dentures herein constitute a well known class of thermosetting resins. Representative of these resins are those derived from bisphenol A and epichlorohydrin cured with any of a variety of polyamines and specialty epoxy resins such as epoxy cresol novolac resins, epoxy phenyl novolac resins, bisphenol F-derived resins, polynuclear phenol-glycidyl ether-derived resins, cycloaliphatic epoxy resins, aromatic and heterocyclic glycidyl amine resins, tetraglycidylmethylenedianiline-derived resins, triglycidyl-p-aminophenol-derived resins, triazine-based resin and hydantoin epoxy resins. Details of the formulation of hard epoxide polymer-forming compositions and the conditions under which they undergo polymerization are well known matters to those skilled in the art and are fully described in the literature, e.g., Kirk-Othmer *Encyclopedia of Chemical Technology*, Third Edition, Vol. 9, pp. 274 et seq., John Wiley & Sons, Inc. which is incorporated by reference herein. The polyether polyols which can be used in preparing the mouth-engaging soft polyurethane portion of the composite denture herein can be selected from amongst any of the polyether polyols heretofore employed in the preparation of polyurethanes. Such polyols possess two, and preferably, three or more hydroxyl groups. Among the useful polyether polyols are included the poly-(oxypropylene) glycols, the poly-(oxypropylene) poly-(oxyethylene) glycols, the poly-(1,4-oxypropylene) glycols and graft copolymers of the poly-(oxypropylene) (polyoxyethylene) glycols with acrylonitrile or mixtures of acrylonitrile and styrene. The equivalent weight of these polyether diols can range between 200 to 100 with a preferred range of 200 to 400. The polyol may consist of simple polyfunctional alcohols such as glycerine, trimethylolpropane, 1,2,6-hexanetriol, or pentaerythritol, or they may consist of polyether triols such as poly-(oxypropylene) or poly(oxyethylene) adducts of the above polyols. The equivalent weight of the polyether polyols may range between 100 to 800 with a preferred range of 100 to 500. It is also understood that various combinations of diols and polyols may be used.

The polyisocyanates used for the preparation of the soft polyurethane elastomers must contain the isocyanate groups directly bonded to the aliphatic moieties thereof. Such isocyanates include, but are not limited to 4,4'-Dicyclohexylmethane diisocyanate, isophorone diisocyanate, 2,2,4-trimethyl-1,6-hexane diisocyanate, hexamethylene diisocyanate, xylylene diisocyanate, "dimeryl" diisocyanate, methylcyclohexyl diisocyanate and the reaction product of 3 moles of hexamethylene diisocyanate with one mole of water (Desmodur N-triisocyanate).

The ratio of NCO to OH in the preparation of the soft isocyanate-terminated prepolymer may range between 1.75 to 2.5 with a preferred range of 2.0 to 2.25. The soft isocyanate-terminated prepolymers should have a free NCO content of about 3.5 to 5.5 percent, preferably, 3.7 to 4.7 percent.

For curing (crosslinking) of the prepolymers, preferred polyols are tertiary amine-containing polyols such as poly(oxypropylene) or poly(oxyethylene) adducts of diamines or triamines, such as ethylenediamine, diethylene triamine, tolylenediamine, phenylenediamine, or aniline, or any diols, polyols or their blends. Advantageously, they are polyols of relatively low molecular weight such as are obtained by condensing propylene oxide with ethylenediamine or pentaerythritol to a molecular weight of about 500, or of trimethylolpropane or any other base compound to a molecular weight up to 2500.

Another preferred curing or crosslinking agent is a hydroxyl-terminated prepolymer. These are prepared essentially the same way as the isocyanate-terminated prepolymers but the ratio is such that there are free and un-reacted hydroxyl groups. The same diols and polyol and isocyanates can be used, though it is preferred that the prepolymer have a functionality greater than 2, which can be obtained by using a polyol having a functionality greater than 2 and/or an isocyanate having a functionality greater than 2. Advantageously, the isocyanate is 2,2,4-trimethyl-1,6-hexane diisocyanate, hexamethylene diisocyanate or Desmodur N.

The ratio of OH/NCO in the hydroxyl-terminated prepolymers advantageously may be in the same range as the NCO/OH ratio in the isocyanate-terminated prepolymers. It will be understood, however, that inasmuch as the crosslinking agent may consist of one or more diols or polyols (no isocyanate), the ultimate OH/NCO ratio is infinity.

Another preferred curing or crosslinking agent is a prepolymer-polyol blend. Thus, a polyurethane prepolymer, advantageously, one having neither free NCO nor free OH groups, can be mixed with a polyol, advantageously a polyol having a functionality of more than 2, to form a prepolymerpolyol blend. When such a blend is mixed with an isocyanate-terminated prepolymer in an NCO/OH ratio of greater than 1, crosslinking is effected both through an NCO-OH reaction and through an NCO-urethane reaction.

To join the hard polymer component to the soft polyurethane component, one or both adjoining surfaces is coated with a primer formulation prepared by mixing polyisocyanate with polyol and thereafter the two components are joined. Upon curing of the soft elastomer formulation, a denture will be provided in which the hard and soft elements are permanently bonded to each other.

In order to accelerate the formation of the prepolymers or the cure of the prepolymers with the cross-linking agents, metal catalysts such as tin catalysts, for example, dibutyltin dilaurate and stannous octanoate, can be used.

In the following soft polyurethane resin formulations (all parts by weight) which are illustrative of the invention herein, the ingredients whose properties are given in the Table below were employed.

I. PREPARATION OF PREPOLYMERS (COMPONENTS A)

| FORMULATION 1 | | |
|---|---|---|
| Polymeg 1000[1], 4 moles × 976 | = | 3904 |
| Polymeg 2000[2], 1 mole × 1998 | = | 1998 |
| Hylene W[3], 10 moles × 262 | = | 2620 |
| Dibutyltin dilaurate catalyst | | 1.7 |
| | | 8523.7 |
| Equivalent weight per one NCO | | 852.4 |

[1]Poly (oxytetramethylene) glycol; Mol. wt. 976
[2]Poly (oxytetramethylene) glycol; Mol. wt. 1998
[3]4,4'-dicyclohexylmethane diisocyanate

PREPARATION PROCEDURE

Polymeg 1000 and Polymeg 2000 are charged into the reactor and the mixture heated to 70° C. It is demoisturized in vacuum for 2–3 hours until the evolution of bubbles ceases.

Afterwards a dry nitrogen blanket is applied and the mixture is cooled to 50° 0C. and Hylene is added. The reaction mixture is stirred at 100–120 rpm for at least 30 minutes and watched, for a slight exothermic reaction may ensue. The temperature of the reactor is maintained at 65°–70° C. The catalyst is added in portions in order to speed up the reaction. After 3 hours have elapsed the NCO content is checked using the n-dibutylamine titration method. The NCO content should be in the range of 4.8%. The variation here and elsewhere may be ±5 percent.

When this level of free NCO is reached, the contents of the reactor are cooled and are packaged into one gallon or one quart lined containers. Dry nitrogen is used to maintain an inert atmosphere in the containers which are then tightly closed.

| FORMULATION 2 | | |
|---|---|---|
| Polymeg 1000, 2 moles × 976 | = | 1952 |
| Polymeg 2000, 1 mole × 1998 | = | 1998 |
| Hylene W, 6 moles × 262 | = | 1572 |
| Dibutyltin dilaurate catalyst | | 1.1 |
| | | 5523.1 |
| Equivalent weight per one NCO | | 920.5 |

Preparation procedures are the same as in Formulation 1. The free NCO content of the prepolymer should be 4.5%.

| FORMULATION 3 | | |
|---|---|---|
| Polymeg 2000, 1 mole × 1998 | = | 1998 |
| Polymeg 1000, 1 mole × 976 | = | 976 |
| Hylene W, 4 moles × 262 | = | 1048 |
| | | 4022 |
| Equivalent weight per one NCO | | 1005.5 |

Preparation procedures are the same as in Formulation 1. The free NCO content should be 4.18%.

| FORMULATION 4 | |
|---|---|
| Polymeg 2000 | 1198 |
| Polymeg 1000 | 488 |
| Hylene W | 786 |
| Dibutyltin dilaurate, catalyst | .76 |
| | 3272.76 |
| Equivalent weight per one NCO | 1190 |

PREPARATION PROCEDURE

Poly(oxytetramethylene) glycols, Polymeg 2000 and Polymeg 1000, are charged into a reactor and demoisturized in vacuum for 2–3 hours upon a gentle stirring of 60–120 rpm at 70° C.

The demoisturized glycol mixture is cooled down to 50° C., a dry nitrogen blanket is applied, and diisocyanate (Hylene W) is added. The catalyst is added in portions in order to speed up the reaction.

The charge of the reactor should exotherm. The temperature of the reactants should not be allowed to go over 75° C. After 2–3 hours of the reaction, the NCO content should be checked by the n-dibutylamine titration method. The NCO content should be in the range of 3.3%. If the content of NCO higher than 3.7% is found, the heating should be continued for an additional hour at 70° C. after the addition of a small amount (0.005%) of the catalyst.

The above soft isocyanate-terminated prepolymers are essentially linear.

PREPARATION OF CROSSLINKING AGENTS (COMPONENTS B)

| FORMULATION 5 | |
|---|---|
| Pluracol 355* | 100 g. |
| TiO$_2$ (rutile) | 0.2 g. |
| Dibutyltin dilaurate catalyst | as needed |
| | 100.2 |
| Equivalent weight per one hydroxyl | 125.1 |

*Poly(oxypropylene) derivative of ethylenediamine, Mol. wt. 490

PREPARATION PROCEDURE

All the pigments are dispersed in 5% of the total polyol, Pluracol 355. For dispersion purposes a ball mill or roller mill or any well-dispersing high speed mill can be employed.

Then all of the remainder of the polyol, Pluracol 355, is stirred in. Afterwards the mixture is degassed and demoisturized by applying a vacuum and gentle heating at 60°–70° C.

The catalyst has to be added before application. The amount of the catalyst depends on the type of isocyanate-terminated prepolymer to be used. Usually 0.15–0.35% of the catalyst is added, based on the total weight of the polymer and on the type of the polymer and the reacting groups.

| FORMULATION 6 | |
|---|---|
| 1,4-Butanediol | 450 |
| Pluracol PeP 550* | 500 |
| TiO$_2$ | 1.g. |
| Dibutyltin dilaurate catalyst | as needed |
| | 951. |
| Equivalent weight per one hydroxyl | 68.0 |

*Poly(oxypropylene) adduct of pentaerythritol of about 500 molecular weight

PREPARATION PROCEDURE

All the pigments are dispersed in 5% of the polyols; then all the remainder of the polyols is blended with the pigment dispersion. Afterwards the mixture is demoisturized by applying a vacuum and gentle heating at 60°–70° C.

The catalyst has to be added before application. The amount of the catalyst depends on the type of isocyanate-terminated prepolymer to be used.

Usually for the rigid elastomer formulation the amount of the catalyst is in the range of 0.15–0.25% for the soft elastomer formulation, in the range of 0.30–0.35%.

| FORMULATION 7 | |
|---|---|
| Pluracol PeP 550 | 500 g. |
| TiO$_2$ | 0.5 |
| | 500.5 |
| Equivalent weight per one hydroxyl | 125.1 |

Preparation procedure is similar to the procedure of Formulation 6.

| FORMULATION 8 | |
|---|---|
| Pluracol TP 440 | 420 g. |
| Butanediol | 450 g. |
| TiO$_2$ | 1 g. |
| Dibutyltin dilaurate catalyst | as needed |
| | 871. |
| Equivalent weight per one hydroxyl | 67 |

Preparation procedure is similar to the procedure of Formulation 6.

| FORMULATION 9 | |
|---|---|
| Desmodur N - triisocyanate[1] | 478 |
| Polymeg 650 - | 2112 |
| Pluracol TP 1540[2] | 750 |
| TiO$_2$ | 5.0 |
| Yellow No. 6 Lake | 3.0 |
| Red No. 3 Lake | 1.8 |
| Blue No. 1 Lake | 0.2 |
| | 3350.0 |
| Equivalent weight per one hydroxyl | 668 |

[1](three moles of hexamethylene diisocyanate reacted with one mole of water)
[2]Poly(oxypropylene) derivative of trimethylolpropane, Mol. Weight 1500

PREPARATION PROCEDURE

Poly(oxytetramethylene) glycol is charged into a reactor and demoisturized in vacuum for 2–3 hours upon gentle stirring at 60–120 rpm at 70° C. Then the vacuum is released under dry nitrogen, and the dry nitrogen blanket is retained during the reaction time.

Desmodur N-triisocyanate is stirred in and reacted with the glycol until the NCO content is reduced to zero. Then Pluracol TP 1540 is blended in.

The pigments are dispersed in a small amount of the triol, Pluracol TP 1540, and stirred in with the total content of the prepolymer-polyol blend.

II. PREPARATION OF SOFT POLYURETHANE RESINS

EXAMPLE 1

Component A, Formulation 1, 100 parts
Component B, Formulation 5, 13.6 parts
Catalyst, stannous octoate, 8 drops
NCO/OH = 1.08 to 1

Components A and B are degassed and demoisturized for at least 1 hour at 60° C. and then blended gently with the catalyst and placed in a pre-heated vacuum oven for 1–2 minutes. They are then cast into a pre-heated denture mold containing a previously cast hard-non-hydrophylic polyurethane elastomer as above described and kept in an oven at 90° C. for 3 hours. The denture is then removed from the mold and finished by removing the sprues and flash and polishing as necessary.

EXAMPLE 2

Component A, Formulation 2, 100 parts
Component B, Formulation 6, 7 parts
Catalyst, dibutyltin dilaurate, 12 drops
NCO/OH = 1.05 to 1

EXAMPLE 3

Component A, Formulation 3, 100 parts
Component B, Formulation 6, 6.44 parts
Catalyst, dibutyltin dilaurate, 16 drops
NCO/OH = 1.05 to 1.

The compositions of Examples 2 and 3 are degassed, demoisturized, blended, cast, and cured as in Example 1.

EXAMPLE 4

Component A, Formulation 9, 100 parts
Component B, Formulation 11, 56.2 parts
Catalyst, stannous octoate, 0.32
NCO/OH = 1.05 to 1.

Components A and B should be heated up to approximately 60° C. and degassed and demoisturized under vacuum before blending. Then the catalyst should be added. The blend should be cast into a preheated mold and heated with a mold release agent. The elastomer should be cured in an oven at 95° C. for 2 hours.

IV. MANUFACTURE OF COMPOSITE DENTURE

EXAMPLE 5

In this example, a pre-formed hard acrylic denture supplied by a dental laboratory or dentist is provided with a mouth-engaging portion prepared with a soft polyurethane elastomer such as any of those described in Examples 1 to 4 above.

The hard acrylic denture is placed in a flask such that the lowest portion of the denture is even with the flask. Investment material is then introduced into the flask even with the top of the flask. After the investment has set-up, a mold release agent is applied to all surfaces, i.e., investment, denture and teeth. After the mold release agent has dried (approximately five minutes), additional investment material is applied to cover the entire denture. The flask is then completely sealed by fastening a lid thereon. The flask is separated and the denture removed. The denture is then ground out to provide room for the soft polyurethane elastomer mouth-engaging portion.

Upon receipt of a conventional, complete acrylic denture with a new rebase impression taken by a dentist, a plaster model is prepared in accordance with conventional dental laboratory procedures. Thereafter, the plaster model is sealed (i.e., a coating is placed on all exposed plaster surfaces except the bottom). The denture is then placed in a flask such that the lowest portion of the denture is even with the flask. Investment material is then introduced into the flask even with the top of the flask. After the investment has set-up, a mold release agent is applied to all surfaces, i.e., investment, denture and teeth.

After the primer or mold release agent has dried (approximately five minutes), additional investment material is applied to cover the entire denture. The flask is then completely sealed by fastening a lid thereon. The flask is separated and the denture removed. The denture is then ground out to provide room for the soft polyurethane elastomer. Sealer is again applied to all newly exposed plaster surfaces. Following the grinding out of the denture, the denture is washed with anhydrous isopropanol or ethanol to remove grinding residue and air-dried. A primer, e.g., 7.8 g Pep 550 (a polyether polyol from BASF Wyandotte having an average molecular weight of about 600 and a hydroxyl number of 448 and which is based on pentaerythritol oxyalkylated with propylene oxide) mixed with 7.3 g Hylene W (DuPont's 4,4'-dicyclohexylmethane diisocyanate) is applied to all surfaces of the denture where the soft elastomer is to adhere. The blockout material is removed from the plaster model. Mold release is again applied to the mold and plaster model and permitted to air-dry (approximately five minutes). The primed denture is then inserted in the mold cavity. Liquid soft polyurethane formulation is introduced into the mold cavity and low spots on the plaster mold. The entire mold assembly is placed in a clamp and the clamped mold is placed in an oven heated to 85° C. After about three hours, the assembly is removed from the oven and cooled until comfortable to the touch. The mold is opened and the denture is removed from the investment and plaster model. The denture is thereafter trimmed, polished, etc., to provide the finished product.

It is to be understood that the invention is not to be limited to the exact details of operation or structure shown and described as obvious modifications and equivalents will be apparent to one skilled in the art.

What is claimed is:

1. An artificial denture of composite construction which comprises a pre-formed tooth-holding portion which has been ground out to provide room for a mouth-engaging portion integrally chemically bonded to said tooth-holding portion, said tooth-holding portion being fabricated from a hard non-polyurethane polymer having a hardness of not less than about Shore D40 selected from the group consisting of a hard acrylic polymer and a hard epoxide polymer and a mouth-engaging portion being fabricated from a soft non-hydrophilic polyurethane elastomer having a hardness of not greater than about Shore A65, said polyurethane being the reaction product of a polyether polyol and an aliphatic, cycloaliphatic or aralkyl di- or polyisocyanate in which the isocyanate groups are directly bonded to the aliphatic, cycloaliphatic or alkyl moieties thereof.

2. The artificial denture of claim 1 in which the hard acrylic polymer or hard epoxide polymer has a hardness of up to Shore D100.

3. The artificial denture of claim 1 in which the di- or polyisocyanate is selected from the group consisting of 4,4'-dicyclohexylmethane diisocyanate, isophorone diisocyanate, 2,2,4-trimethyl-1,6-hexane diisocyanate, hexamethylene diisocyanate, xylylene diisocyanate, dimeryl diisocyanate, methylcyclohexyl diisocyanate and the reaction product of 3 moles of hexamethylene diisocyanate with one mole of water.

4. The artificial denture of claim 1 in which the polyether polyol is a polyether diol, triol or tetrol having an equivalent weight of 100 to 800.

5. The artificial denture of claim 4 in which the polyol is derived from pentaerythritol or glycerol oxyalkylated with ethylene oxide, propylene oxide or a mixture thereof.

6. The artificial denture of claim 1 in which the hard polymer is integrally chemically bonded to the polyurethane elastomer with a polyurethane-based primer.

7. The artificial denture of claim 1 in which the soft non-hydrophilic polyurethane elastomer contains no plasticizer.

* * * * *